United States Patent
Speier et al.

(10) Patent No.: US 12,201,457 B2
(45) Date of Patent: Jan. 21, 2025

(54) ASSIGNMENT OF MR IMAGES TO CARDIAC PHASES

(71) Applicants: Siemens Healthineers AG, Forchheim (DE); Guy's & St. Thomas' NHS Foundation Trust, London (GB)

(72) Inventors: Peter Speier, Erlangen (DE); Peter Gatehouse, London (GB)

(73) Assignees: Siemens Healthineers AG, Forchheim (DE); Guy's & St. Thomas' NHS Foundation Trust, London (GB)

( * ) Notice: Subject to any disclaimer, the term of this patent is extended or adjusted under 35 U.S.C. 154(b) by 175 days.

(21) Appl. No.: 17/897,767

(22) Filed: Aug. 29, 2022

(65) Prior Publication Data

US 2023/0079852 A1   Mar. 16, 2023

(30) Foreign Application Priority Data

Aug. 31, 2021   (EP) .................................... 21194084

(51) Int. Cl.
*A61B 5/055*   (2006.01)
*A61B 5/00*    (2006.01)
(Continued)

(52) U.S. Cl.
CPC .......... *A61B 5/7289* (2013.01); *A61B 5/0265* (2013.01); *A61B 5/055* (2013.01);
(Continued)

(58) Field of Classification Search
CPC .......... G01R 33/56325; G01R 33/5673; A61B 5/0265; A61B 5/055; A61B 5/33; A61B 5/352; A61B 5/36; A61B 5/7289
See application file for complete search history.

(56) References Cited

U.S. PATENT DOCUMENTS

| 5,997,883 A | 12/1999 | Epstein et al. |
| 2018/0325411 A1 | 11/2018 | Nomura et al. |
| 2018/0353139 A1 | 12/2018 | Speier et al. |

FOREIGN PATENT DOCUMENTS

| EP | 2491858 A1 | 8/2012 |
| EP | 3413075 A1 | 12/2018 |

OTHER PUBLICATIONS

Wikipedia "QT interval" Date of screenshot: Feb. 10, 2021.
(Continued)

*Primary Examiner* — Mark D Remaly
(74) *Attorney, Agent, or Firm* — Harness, Dickey & Pierce, P.L.C.

(57) ABSTRACT

A method includes determining a heart beat signal during acquisition of MR images obtained at a plurality of cardiac cycles; determining at least one physiological parameter of a heart obtained at the plurality of cardiac cycles; determining a model including, determining, in each of the cardiac cycles, a variable time interval of variable duration and at least one additional time interval based on the heart beat signal and the at least one physiological parameter, the at least one additional time interval having a lower variability in duration than the variable time interval; determining a duration of the variable time interval and a duration of the cardiac cycle for each of the cardiac cycles based on the heart beat signal and the at least one physiological parameter; and assigning the MR images to the different cardiac phases based on the variable time interval and each of the cardiac cycles.

19 Claims, 8 Drawing Sheets

(51) Int. Cl.
  *A61B 5/0265*  (2006.01)
  *A61B 5/33*    (2021.01)
  *A61B 5/352*   (2021.01)
  *A61B 5/36*    (2021.01)

(52) U.S. Cl.
  CPC ............... *A61B 5/33* (2021.01); *A61B 5/352* (2021.01); *A61B 5/36* (2021.01)

(56) References Cited

OTHER PUBLICATIONS

Cross R. et al.: "Improved workflow for quantification of left ventricular volumes and mass using freebreathing motion corrected cine imaging", Cross et al. Journal of Cardiovascular Magnetic Resonance (2016) 18:10.
"Cardiac function and PA pressure" echobasics | free echocardiography tutorial online since 2004 https://echobasics.de@diastole-en.html.
Chung S. et al:"Duration of diastole and its phases as a function of heart rate during supine bicycle exercise", Am J Physiol Heart Circ Physiol 287: H2003-H2008, 2004.
Chung, S. et al: "Improved Method for Retrograde Gating for Cardiac Magnetic Resonance Imaging", Proc. Intl. Soc. Mag. Reson. Med. 20 (2012), S. 3853.
Wikipedia—Isovolumetric contraction: https://web.archive.org/web/20190502072505/https://en.wikipedia.org/wiki/Isovolumetric_contraction (Stand:Feb. 5, 2019).
The Wayback Machine: "Blood Flow", https://web.archive.org/web/20200810145850/http://www.rnceus.com/hemo/bloodflo2.htm, (Stand: Apr. 8, 2022).

ASSIGNMENT OF MR IMAGES TO CARDIAC PHASES

CROSS-REFERENCE TO RELATED APPLICATION(S)

The present application claims priority under 35 U.S.C. § 119 to European Patent Application No. 21194084.6, filed Aug. 31, 2021, the entire contents of which are incorporated herein by reference.

TECHNICAL FIELD

The present application relates to a method for assigning MR images of a heart obtained at a plurality of cardiac cycles to different cardiac phase of the cardiac cycles, to a corresponding module configured to assign the MR images and to a computer program comprising program code. Finally, a carrier comprising the computer program is provided.

BACKGROUND

Cardiac MRI (Magnetic Resonance Imaging) requires synchronization with cardiac motion to avoid image artefacts like blurring or phase-encode ghosting of cardiac tissue. For synchronization, a trigger signal generated from the cardiac motion is used. This signal can be generated by different sources; in clinical use it is usually the ECG, or photoplethysmography if necessary, as this is markedly inferior for reasons given later. More experimental techniques exist, e.g., acoustic triggering or Pilot Tone.

Cine imaging generates an apparent movie loop over the cardiac motion phases (CPh). However, it is important to understand that this is not usually a "real-time" movie. For sufficiently fine spatiotemporal resolution, the standard in clinical use is to acquire the data over typically 4-7 cardiac cycles during a breath hold, by acquiring a fraction of the required raw data (a "block" of kSpace lines of number "segments") in each cycle. For image reconstruction, the blocks are combined to form a series of data sets for each timing after the trigger, complete enough to reconstruct an image series from them. The task is to combine data that corresponds to the same cardiac motion phase so that the series of these sets can support accurate measurement of cardiac function, while also being clear enough to give clinically useful reports on wall motion abnormalities, flow disturbances, valve diseases, etc. which under ideal patient conditions is the "gold standard" imaging of cine CMR.

Those ideal conditions required for conventional retrogated cine include breath-holding and a stable heartrate (to within about 10%) during the breath-hold. While most patients will co-operate with breath-hold requests, in clinical cardiology many have cardiac arrhythmias of one kind or another. Arrhythmias are not rare for cardiac patients and can be present in maybe one out of five patients. If the heartbeats regularly during the acquisition, the blocks can be selectively combined for FFT of each cine frame image based on their acquisition time relative to the last trigger signal (TT or time-after-trigger) because the relationship between TT and CPh is the same in every heartbeat. In practice however, this assumption is often violated when the cardiac cycles during the breath-hold varied in duration, e.g., due to clinical arrhythmias or even simply due to heart rate tending to change during a breath-hold. For example, in respiratory sinus arrhythmia, a normal effect that is stronger in the young or athletic, the heart rate tends to decrease during the expiratory breath-hold (expiration is typically used for CMR because of its more reproducible position than inspiration).

Thus, data blocks or segments corresponding to the same CPh have to be determined. If a high quality continuous monitoring of the cardiac phases for every heartbeat is available—sources could be ultra-sound, Pilot Tone diagnostic ECG, then the CPh can be determined from these monitoring signals directly.

However, these signals are typically not available with sufficient quality and thus a model f(TT,RR) that maps from TT to CPh in each cardiac cycle can be used. This model can also be seen as a heartbeat specific correction of the TT, i.e., an interpolation from measured TT to normalized TT(NTT) where NTT is adapted to a representative mean cardiac cycle duration (MCD) which itself is derived over the duration of the breath-hold e.g., the mean or median value of all CCD during the breath-hold.

The simplest model is linear interpolation. This is used in retrogating measurements: For the raw data in each cardiac cycle, the trigger time TT(R) after the R-wave PMU trigger event is normalized by the current cardiac cycle's duration CCD to yield a linear model estimation of the cardiac phase, $$CPh = TT(R)/CCD; \quad [1]$$

where CPh runs from 0 to 1 in each cycle, performing a linear stretch function for cycles where CCD is shorter than other cycles. This method has drawbacks. It is known that heart motion does not simply scale linearly as above (i.e. a simple "affine stretch" operation uniformly throughout the cycle) with changes in the total cardiac cycle length. Instead, different cardiac phases scale differently. The main effect known from literature is that the time TQT from the ECG Q-wave, which immediately precedes the R-wave, to the end of the T-wave, depends only slightly on CCD. Mechanically this interval corresponds to the time of ventricular contraction onset to the complete relaxation of the ventricle. Wikipedia lists several scientific models for this relationship: A good approximation is a linear relationship (Sagie's equation) where TQT increases by only 2% if the heart rate 1/CCD decreases by 10 bpm (bpm=beats per minute), i.e., by 16% of a 60 bpm heartrate.

If it is assumed that the heart rate does not change excessively (say 25%, so the TQT change of 3% may be considered negligible) during a breath hold scan, then one can use a fixed value for TQT and use linear interpolation of the cardiac phase for only the varying time outside the TQT. Employing this distributed scaling of the heart cycle is known. A mathematical summary of the distributed scaling is presented below.

The following equation 2 describes this behavior:

$$[2] \; CPh = \{ \\ ((TT(R) - TQT)*(MCD - TQT) / (CCD - TQT) \\ + TQT) / MCD \text{ for } TT(R) > TQT \\ TT(R)/MCD \\ \text{for } TT(R) < TQT \\ \}$$

With MCD being the representative mean cycle duration and CCD the current cycle duration.

Note 1: The form of the equation for TT(R)>TQT gives CPh=1 when TT(R)=CCD and CPh=TQT/MCD when TT(R)=TQT, where it joins up ok with the TT(R)<TQT form of the equation.

Note 2: When these equations are applied in practice to ECG based R-wave triggering, the time TQR between Q- and R-wave is considered negligible and TRT is used in place of TQT, i.e., the non-scaling interval is taken to begin at the ECG trigger time point, the R-wave. This assumption is questionable, because the QR interval often lengthens in cardiac patients.

In addition, ECG based trigger time points in MR lag behind the R-wave onset, because the ECG detects the R-peak maximum and also has a processing lag due to internal data filtering. These delays are typically ignored and in prior art the above equation is applied using R-wave triggering.

Other trigger mechanisms than ECG will trigger even later, e.g., a plethysmographic trigger will be delayed by the time the pulse wave takes to travel from the heart to the finger time, typically on the order of 200 ms, cardiac triggering using Pilot Tone is sensitive to the heart motion, and can be robustly achieved by triggering only after the contraction has started.

phonocardiogram has been used mainly at magnetic fields>3T where ECG triggering is more difficult, but the extra technology required and considerable difficulty under gradient acoustic noise of cine imaging are believed to rule this out, and anyway its most prominent trigger (the second heart sound) is delayed about 300 ms and can be affected by valve disease.

An improvement over the model in equation to is described in Chung Storey and Axel (ISMRM 2012 #3853 [Chung2012]). The authors propose to modify the dual interval model of equation 2 for ECG triggering and limited the linear scaling part to diastasis. They used ad hoc parameters for the duration of the fixed interval before and after the trigger with 300-400 ms and 50-150 ms respectively, depending on RR, and demonstrated improved image quality in 4 patients.

A physiologic foundation for this model can be found in e.g., Chung C S, Karamanoglu M, Kovacs S J. Duration of diastole and its phases as a function of heart rate during supine bicycle exercise. Am J Physiol Heart Circ Physiol. 2004 November; 287(5):H2003-8. doi: 10.1152/ajp-heart.00404.2004. Epub 2004 Jun. 24. PMID: 15217800 [Chung2004].

The part of the cardiac cycle that scales with CCD is even shorter than the (CCD-TQT) assumed in equation 2. Using ultra-sound the authors concluded that the invariant unscaled portion of the CCD extends beyond the TQT time for two reasons: the duration of the early diastolic filling (ventricular expansion) interval (=ultra-sound E-wave (for "early filling") which starts with the ECG T-wave), and also the duration of the atrial contraction interval (ultra-sound: A-wave, starting with ECG P-wave or with Pilot tone signal maximum): both of these extension intervals beyond TQT are essentially independent of CCD.

SUMMARY

This only leaves the mid-diastolic true resting interval (hereafter called "diastasis") to scale with CCD. This linear scaling interval is starting with the end of the ultra-sound E-wave and ends with the start of the ultra-sound A-wave.

The model in Chung2012 has the drawback that it uses adhoc values for its parameters. These might have been derived from literature, e.g., [Chung2004], but are not adapted to the individual patient and clinical conditions are known to result in significantly different values.

Accordingly, a need exists to optimize cardiac phase interpolation in a patient.

It is also an aim to provide an interpolation rule not only for ECG based R-wave triggering, but for arbitrary trigger time points in the cardiac cycle.

This need is met by the features of the independent claims. Further aspects are described in the dependent claims.

According to one or more example embodiments, a method for assigning MR images of a heart obtained at a plurality of cardiac cycles to different cardiac phases of the cardiac cycles, the method comprising determining a heart beat signal during acquisition of the MR images obtained at the plurality of cardiac cycles; determining at least one physiological parameter of the heart during acquisition of the MR images obtained at the plurality of cardiac cycles; determining a model for the cardiac cycle, the determining the model including, determining, in each of the cardiac cycles, a variable time interval of variable duration and at least one additional time interval based on the heart beat signal and the at least one physiological parameter, the at least one additional time interval having a lower variability in duration than the variable time interval; determining a duration of the variable time interval and a duration of the cardiac cycle for each of the cardiac cycles based on the heart beat signal and the at least one physiological parameter; and assigning the MR images to the different cardiac phases based on the duration of the variable time interval and cardiac cycle in each of the cardiac cycles.

According to one or more example embodiments, the determining the at least one physiological parameter determines the at least one physiological parameter based on a magneto-hydrodynamic effect of blood flow occurring in each of the plurality of cardiac cycles.

According to one or more example embodiments, the heart beat signal is an ECG signal, and the determining the duration of the variable time interval includes determining an end of an early passive filling of a ventricle in a diastole and a first particular time interval between a Q wave of the ECG signal and the early passive filling of the ventricle, wherein the duration of the variable time interval is based on the first particular time interval.

According to one or more example embodiments, the determining the duration of the variable time interval includes determining a second particular time interval between a P wave and the Q wave of the ECG signal.

According to one or more example embodiments, the determining the at least one additional time interval determines the at least one additional time interval based on the first particular time interval and the second particular time interval.

According to one or more example embodiments, the determining the at least one additional time interval determines the at least one additional time interval based on a combination of the first particular time interval and the second particular time interval.

According to one or more example embodiments, the determining the variable time interval determines the variable time interval based on a corresponding cycle duration of a total cardiac cycle minus a duration of the determined at least one additional time interval for each of the cardiac cycles.

According to one or more example embodiments, the determining the duration of the variable time interval includes determining a third particular time interval between the Q wave of the ECG signal of the heart and an R wave of the ECG signal as a start point of a duration of at least one of the cardiac cycles, wherein the determining the duration of the variable time interval determines the variable time interval based on the third particular time interval.

According to one or more example embodiments, the determining the variable time interval includes determining the Diastasis as one of the cardiac phases in the cardiac cycle.

According to one or more example embodiments, the determining the at least one physiological parameter determines the at least one further physiological parameter based on at least one of an ECG signal, a pilot tone, acoustic signals of the heart, and the MR images obtained from the heart.

According to one or more example embodiments, the determining the model includes for each of the cardiac cycles, determining a total duration of the cardiac cycle based on R waves in an ECG signal, wherein the total duration comprises two interpolation periods of constant duration and the variable time interval, wherein the determining the duration of the variable time interval determines the duration of the variable time interval based on the duration of the two interpolation periods and the total duration.

According to one or more example embodiments, the duration of the two interpolation periods is based on a first particular time interval between a Q wave of the ECG signal and an early passive filling of a ventricle, a second particular time interval between a P wave and the Q wave of the ECG signal and a third particular time interval between the Q wave of the ECG signal of the heart and an R wave of the ECG signal.

According to one or more example embodiments, module is configured to assign MR images of a heart obtained at a plurality of cardiac cycles to different cardiac phases of the cardiac cycles, the module comprising at least one processor; and a memory containing instructions executable by the at least one processor, wherein the at least one processor is configured to execute the instructions to cause the module to, determine a heart beat signal during acquisition of the MR images obtained at the plurality of cardiac cycles, determine at least one physiological parameter of the heart during acquisition of the MR images obtained at the plurality of cardiac cycles, determine a model for the cardiac cycle including determining, in each of the cardiac cycles, a variable time interval of variable duration and at least one additional time interval based on the heart beat signal and the at least one physiological parameter, the at least one additional time interval having a lower variability in duration than the variable time interval, determine a duration of the variable time interval and the duration of the cardiac cycle for each of the cardiac cycles, and assign the MR images to the different cardiac phases based on the duration of the variable time interval and cardiac cycle in each of the cardiac cycles.

According to one or more example embodiments, a non-transitory computer readable medium comprises program code that, when executed by at least one processor, causes the at least one processor to carry out the method according to one or more example embodiments.

BRIEF DESCRIPTION OF THE DRAWINGS

The foregoing and additional features and effects of the invention will become apparent from the following detailed description when read in conjunction with the accompanying drawings in which like reference numerals refer to like elements.

DETAILED DESCRIPTION

Figure 1:
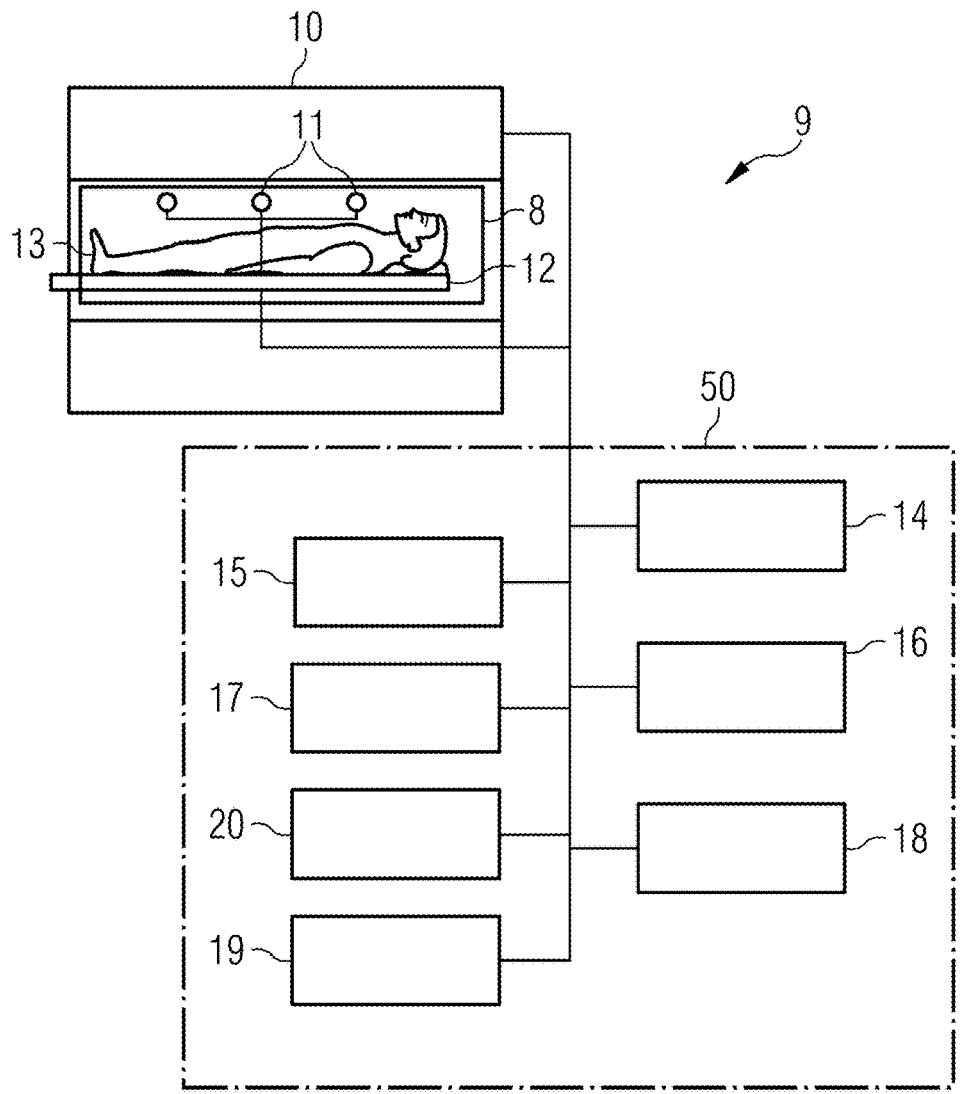
FIG. 1 shows a schematic view of an MR imaging system configured to generate MR images of the heart and to assign them to different phases of the cardiac cycle according to at least one example embodiment.

According to a first aspect a method for assigning MR images of a heart obtained at a plurality of cardiac cycles to different cardiac phases of the cardiac cycles is provided. The method comprises the step of determining a heart beat signal during the acquisition of the MR images obtained at the plurality of cardiac cycles. Furthermore at least one physiological parameter of the heart is determined during acquisition of the MR images obtained at the plurality of cardiac cycles.

A heart beat signal may refer to a measurement signal encoding a (specifically periodic) movement of a heart, and may include, for example one of an ECG measurement signal, a pulse measurement signal such as a pressure or optical or acoustic measurement signal, a continuous RF signal representing cardiac motion received simultaneously during a MRI measurement (PilotTone measurement signal), wherein the measurement signals may include characteristics caused by a cardiac movement, and thereby describe or represent a cardiac movement, in particular a periodic cardiac movement, and such may be used for determining cardiac cycles and/or phases.

A model for the cardiac cycle is determined wherein, in each of the cardiac cycles, a variable time interval of variable duration, and at least one additional time interval with a lower variability in duration than the variable time interval is determined based on the heart beat signal and the at least one physiological parameter. A duration of the variable time interval and the length of the cardiac cycle is determined for each of the cardiac cycles based on the heart beat signal, specifically an ECG signal, and the at least one physiological parameter, and the MR images are assigned to the different cardiac phases taking into account the duration of the variable time interval and cardiac cycle in each of the cardiac cycles.

The present method discussed above combines all information available in the MR system about real-time beat-to-beat physiology to optimally and individually adjust the durations of the cardiac cycles for each cycle and the MR images or raw data obtained during the different cardiac cycles.

The at least one physiological parameter is preferably determined based on a magneto-hydrodynamic effect of blood flow occurring in each of the plurality of cardiac cycles. The magneto-hydrodynamic effect helps to precisely determine and differentiate the variable time interval and the additional time interval in each cycle.

Preferably, for determining the length of the variable time interval an end of an early passive filling of a ventricle in the diastole is determined and a time interval TQE (a first particular time interval) between a Q wave present in the ECG signal and the early passive filling of the ventricle, wherein the length of the variable time interval can determined taking into account the time interval TQE.

Furthermore, it is possible, for determining the length of the variable time interval, to determining a time interval TPQ (a second particular time interval), between a P wave and a Q wave present in the ECG signal.

The at least one additional time interval might be determined based on the time interval TQE and the time interval TPQ. The time intervals TQE and TPQ may be combined to determine the at least one additional time interval.

The variable time interval can be determined, for each of the cardiac cycles, based on a corresponding total cardiac cycle duration minus the length of the determined at least one additional time interval. The total cardiac cycle duration may be determined from the heart beat signal, specifically the ECG signal, e.g. the R wave or from any other signal.

The determination of the length of the variable time interval can include determining a time interval TQ0 (a third particular time interval) between a Q wave of the ECG signal of the heart and the R wave of the ECG signal as start point of a duration of the cardiac cycle, wherein the length of the variable time interval is determined taking into account the time interval TQ0.

When the variable interval is determined, it is possible to determine the Diastasis as one of the cardiac phases in the cardiac cycle.

The at least one further physiological parameter can be determined based on the heart beat signal, specifically at least one of an ECG signal, a pilot tone, acoustic signals of the heart, and MR images obtained from the heart.

For each of the cardiac cycles, a total duration of the cardiac cycle CCD can be determined based on the R waves in the ECG signal, wherein the total duration comprises two interpolation periods of constant length and the variable time interval, wherein the length of the variable time interval is determined based on the duration of the 2 interpolation periods and the total duration.

The duration of the 2 interpolation periods can be determined based the time interval TQ0, the time interval TQE, and the time interval TPQ.

Furthermore, a module configured to assign a plurality of cardiac cycles to different cardiac phases of the cardiac cycles is provided which is configured to operate as discussed above or as discussed in further detail below.

Furthermore, a computer program comprising program code to be executed by at least one processing unit of the entity is provided, wherein execution of the program code causes the at least one processing unit to carry out a method as discussed above or as discussed in further detail below.

Additionally a carrier comprising the computer program is provided wherein the carrier is one of an electronic signal, optical signal, radio signal, and computer readable storage medium.

It is to be understood that the features mentioned above and features yet to be explained below can be used not only in the respective combinations indicated, but also in other combinations or in isolation without departing from the scope of the invention.

Features of the above-mentioned aspects and embodiments described below may be combined with each other in other embodiments unless explicitly mentioned otherwise.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are to be illustrative only.

The drawings are to be regarded as being schematic representations and elements illustrated in the drawings are not necessarily shown to scale. Rather, the various elements are represented such, that their function in general purpose becomes apparent to a person with skill in the art. Any connection or coupling between functional blocks, devices, components of physical or functional units shown in the drawings and described hereinafter may be implemented by an indirect or direct connection. A coupling between components may be established over a wired or wireless connection.

Functional blocks may be implemented in hardware, software, firmware, or a combination thereof.

A simple method in the case of extreme infrequent outliers in CCD is known where data from cardiac cycles whose duration lies outside a user-specified acceptance window is reacquired. This may be effective in cases of infrequent arrhythmias, less than about 1 beat in 5 where all other CCD lie within the acceptance range. Most clinical users find this of limited practicability, especially as quite correctly this method rejects not only the abnormal CCD but also the CC following the abnormal CC on the basis of abnormal time for blood to refill the heard. The "arrhythmia rejection by time" method is less useful with more frequent irregularities or respiratory sinus arrhythmia, where it unpredictably, and usually greatly, extends the breath-hold time required, which users find impracticable.

Another cardiac MRI technique also used for the challenge of cardiac arrhythmia is real time cine imaging, which is inherently of inadequate resolution, but considerably successful when assisted by compressed sensing for approximate cardiac function measurements. However, real-time (unsegmented) compressed sensing cines degrade the truly obtained (as opposed to the fine stated "fitted") spatiotemporal resolution, such that real-time CS cines are unsatisfactory for many clinical applications such as wall motion abnormalities and valve disease among others. For these applications segmented acquisition is still required to yield the reputed "gold standard" quality of conventional CMR.

Another approach used in clinical work is to setup segmented cine imaging under free-breathing with averaging, aiming to average over the respiratory and cardiac variations. This is often surprisingly effective but of course tends to be slower to acquire and also cannot be targeted on small features which may move too much with respiration.

FIG. 1 shows a schematic view of an MR imaging system 9, which comprises a magnet 10 generating the magnetic field B0 and which can generate the MR images of the heart which should be assigned in a retroactive gating to the different cardiac phases of the cardiac cycle. The patient or object under examination 13 lying on a table 12 is moved into the center of the MR imaging system 9, where the MR signals can be detected after excitation by RF pulses using coils 11. By applying RF pulses and magnetic field gradients, the nuclear spins of object 13, especially the part located in the receiving coils are excited and location coded currents induced by relaxation can be detected. The way how MR images, especially CINE images are generated and how the MR signals are detected, using a sequence of RF pulses and a sequence of magnetic field gradients, is known in the art, so that a detailed explanation thereof is omitted. The MR system may furthermore comprise shim coils 8 which are used to correct in-homogeneities of the magnetic field B0.

The MR imaging system 9 comprises a control module 50 which is used for controlling the MR imaging system. The control module 50 comprises a gradient control unit 14 for controlling and switching the magnetic field gradients, an RF control unit 15 for controlling and generating RF pulses for the imaging sequences. The image sequence control unit 16 is provided to control the sequence of the applied RF pulses and magnetic field gradients and thus is also configured to partly control the gradient control unit 14 and the RF control unit 15. In a memory 17, computer programs needed for operating the MR imaging system and the imaging sequences necessary for generating the MR images can be stored together with the generated MR images. The MR images and any further information can be displayed on a display 18 wherein a human machine interface 19 is provided, which can be used by an operator of the MR imaging system to control the MR imaging system. A central processing unit 20 can coordinate the operation of the different functional units shown in FIG. 1 and can comprise one or more processors, which can carry out instructions stored on the memory 17. The memory can include program code to be executed by the processing unit 20.

In the following, the different steps carried out during the assignment of the MR images to the different phases are discussed in more detail.

In the example below, an interpolation model is discussed to reduce the dimensionality of the interpolation problem. The simplest choice is based on [Chung2004] and [Chung2012]: A two interval model is selected with one interval of constant duration, also called additional time interval, and one interval scaling with RR for an arbitrary trigger time point at a time TP0 after the P-wave, also called variable time interval. Relative to a trigger at an arbitrary point in the cardiac cycle during the first interval that does not coincide with the P-wave, the cardiac cycle is divided in at least 3 intervals (2 interpolation periods and the variable time interval) with different interpolation rules.

Model Selection

Figure 2:
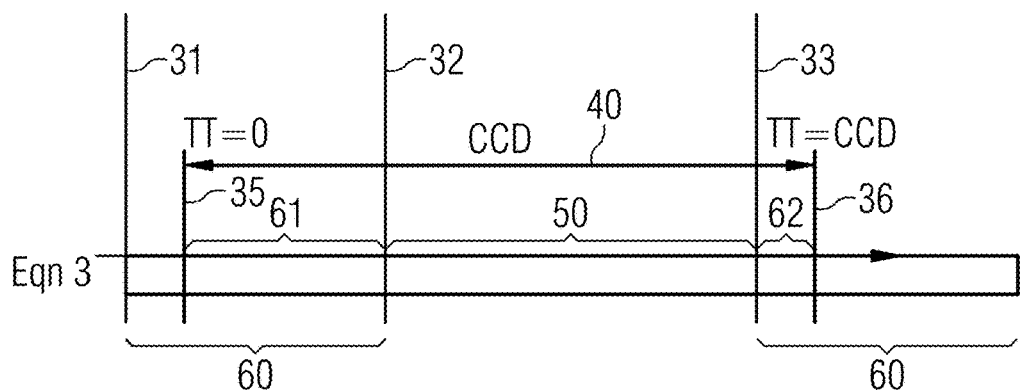
FIG. 2 shows a schematic view of a model used to assign the MR images to the different heart phases according to at least one example embodiment.

FIG. 2 shows a cardiac cycle and how a model is used with a variable time interval that the cycle begins at the trigger time point TT=0 with a weakly scaling interval followed by a linearly scaling interval and ends again with a weakly scaling interval.

FIG. 2 shows the lengths of the cardiac cycle 40 as determined by the R wave of the ECG signal. The two R waves are shown by the time points 35 and 36. Furthermore, the P wave 31 of the ECG signal, the end of the E wave, e.g. determined from an ultrasound signal is shown by 32 and the P wave 33 as determined from the ECG signal is indicated. The model is based on a variable time interval 50 and a constant or additional time interval 60. Based on the trigger points, the cardiac cycle comprises a first interval 61 which is more or less independent of the cardiac cycle, the variable time interval 50 and a part of the consecutive constant time interval, the interval and 62.

Figure 3:
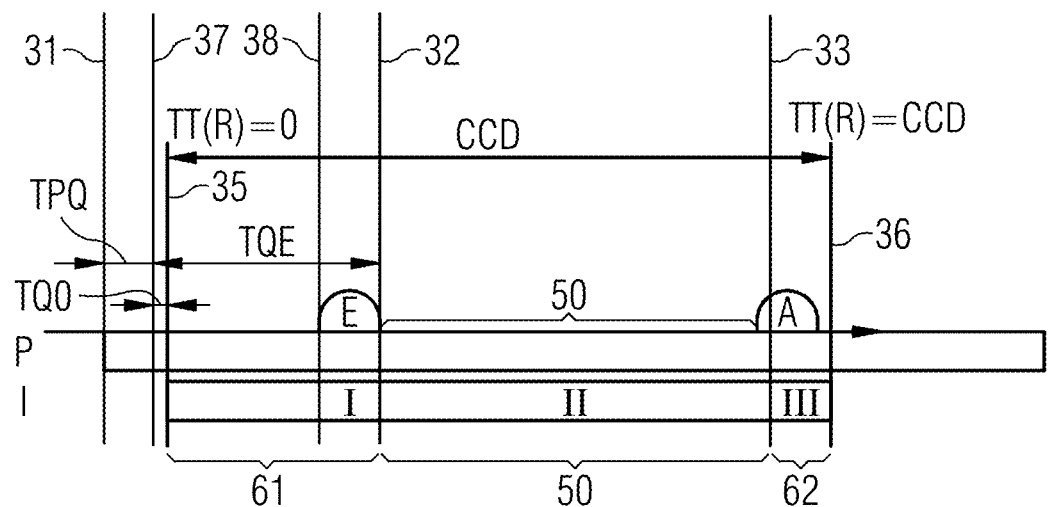
FIG. 3 shows a more detailed view of the model of FIG. 2 and the calculation of the duration of the variable time interval occurring in the cardiac cycle according to at least one example embodiment.

FIG. 3 and the following equation 3 set these intervals or intervals in relation to the physiologic events as seen by ultra-sound and diagnostic ECG. In addition to the time points 31, 32 and 33, discussed in connection with FIG. 2, the following time points are shown: the ECG Q wave 37, and the end of the ECG T wave 38.

FIG. 3 shows the physiological periods P and the interpolation periods I.

Equation [3]

$$CPh = \begin{cases} TT(R) / MCD; & \text{for } TT(R) < T0E, \\ ((TT(R) - T0E) * (MCD - TPE) / (CCD - TPE) + T0E) / MCD & \text{for } T0P > TT(R) > T0E \\ (TT(R) - T0P) / MCD + maxScaledPhase & \text{for } TT(R) > T0P \end{cases}$$

with $$maxScaledPhase = ((TOP - T0E) * (MCD - TPE) / (CCD - TPE) + T0E) / MCD;$$

With
CCD=cardiac cycle duration of the current heartbeat
MCD="average", e.g., mean or median cardiac cycle length over the measurement
T<A><B>=time from event <A> to event <B>
0=trigger time point
E=(end of) ultra-sound E-wave
A=(start of) ultra-sound A-wave
P=ECG P-wave
Q=ECG Q-wave The following relationships hold:

$T0E = TQE - TQ0$ = duration of interval I, shown by reference numeral 61

$TP0 = TPQ + TQ0$ = duration of interval III, shown by reference numeral 62

$TPE = TPQ + TQE$ = weakly scaling interval shown by reference numeral 60

$TEP = CCD - TPE$ = linearly scaling interval (diastasis 50)

$T0E = TQE - TQ0$ $T0P = CCD - TP0 = T0E + TEP$

The model is parametrized fully with the measured cycle durations CCD and MCD and 2 timing parameters. One useful choice for these two parameters would be a purely physiologic parameter, e.g., TPE, giving the total duration of the weakly scaling interval 60 parameter, plus a parameter that contains besides physiological information all system specific times, e.g., TP0 specifying the position of the trigger in the cardiac cycle (from the P-wave as its notation implies). The system specific part of the second parameter can be predetermined once the triggering algorithms have been fixed.

If heartbeats occur with CCD<T0E, they can either be rejected as being non-representative or incorrectly triggered or scaled according to equation 1.

Rough values for the parameters are

TQE~400 ms (−100 ms, i.e. ½ E-wave duration*)
TPQ~150 ms (−70 ms, i.e. ½ A-wave duration*)

Transition between the intervals does not occur instantaneously but occurs smoothly over a time period. Thus, a conservative estimate of their duration should be applied.

Thus, for the model with predetermined constants, we would apply only half their duration (~100 ms for E-wave and ~70 ms for A-wave.)

A further refinement of the parameter choice could take into account that parameters scale with average RR as described in [Chung2003].

These parameters could be used as starting values or to specify a value range for a parameter optimization algorithm.

Alternative Models:
1. Because the underlying mechanical motion can be smooth, the separation into 3 regions with different interpolation rules is just an approximation to the smooth variation likely to occur in reality, so the transitions between regional rules could be gradual rather than instant.
2. a general smooth interpolation rule, e.g., described by splines
3. a closed equation, e.g., arctan(f(TT/CCD))

Measure Model Data

The parameters for the interpolation model are derived from information recorded in the MR scanner. All data that represents cardiac motion and is thus subject to the same scaling rules can be used. This data can be physiological data like ECG, pulse, PT or acoustic signals, or MR imaging data or a combination thereof. Preferably, the data is measured simultaneously with the cine measurement.

This results in an important advance offered by example embodiments of the invention: the interval guidance is measured per heartbeat used and in real-time simultaneously with the cine measurement.

Determine Model Parameter

The physiologic contribution to the parameters can be determined in multiple ways:

a) Parameters from Measured Data

Physiologic monitoring signals like Pilot Tone or MR-navigators or -images can be evaluated for interpolation.

Methods for Data Analysis Include
  running trial reconstructions using interpolations over a predetermined range of parameters and maximizing image sharpness.
  apply equation 2 to physiologic or imaging data, running it forward and backward in time and comparing the resulting signals or images for differences to determine the start and end point of the linear scaling interval.
or a combination of the above methods on different signals b) Literature Parameters The values from literature could be coupled to a measured parameter, e.g., they could be a function of heart rate (prior art) or known clinical condition (new). Literature values can be used as start or boundary values for model fitting, and as model values for a subset of model parameters, e.g., in case of insufficient data quality to determine all model parameters.

c) Interactive Parameters

Finally, the user can override internal parameter values in situations where the user has additional more accurate information, e.g., from ultra-sound, diagnostic ECG or high-resolution MR cine measurements.

Apply Parametrized Model

MR data contains for every readout the time-after-trigger TT. The model is applied to these timestamps to map MR data from different cardiac cycles to a common coordinate system, i.e., the cardiac phase CPh.

Inaccuracies of the model and its parametrization could result in interpolation errors that cause inconsistencies between the data from different heartbeats. This will result in image artefacts like blurring or ghosting. These interpolation errors increase with time from the trigger point. Using standard forward interpolation these errors could thus affect the late diastolic images most. These errors can be minimized by keeping the interpolation distance small. Interpolating backward from the end of the cardiac cycle instead of forward from the beginning, the error can be minimized in the late diastolic portion of the cardiac cycle. Thus, it is beneficial to apply both interpolation directions and merge the results from both interpolation directions. Interpolation can be achieved by forming a weighted average of the resulting values for CPh with smoothly varying weights across the cardiac cycle.

More options how the physiological parameter is deduced from the acquired data are described in the application having the title "Using cardiac motion for training a cardiac phase" from the same inventors as the present application and filed on the same day as the present application.

Figure 4:
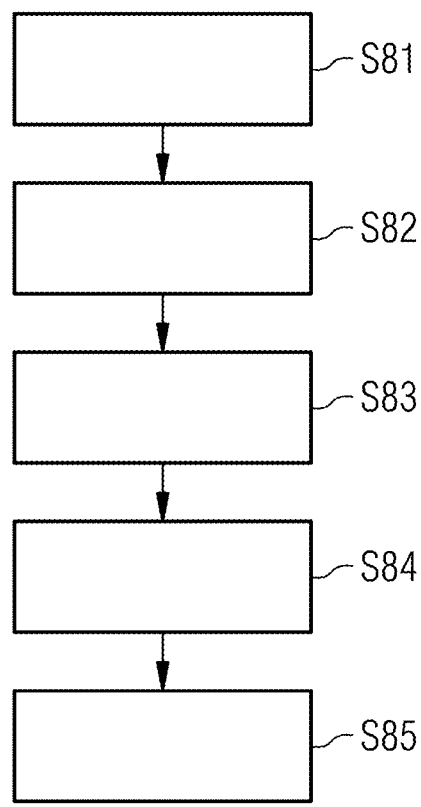
FIG. 4 shows a schematic view of a flowchart comprising the steps needed for assigning the MR images to the different phases of a cardiac cycle according to at least one example embodiment.

FIG. 4 summarizes some of the steps which are carried out in the method discussed above.

In step S 81 that ECG signal is determined during the acquisition of the MR images which are obtained at the different cardiac cycles. Furthermore, in step S 82, at least one physiological parameter of the heart is determined during the acquisition of the MR images which are obtained at the different cardiac cycles. Furthermore, in step S 83 a model is determined for the cardiac cycle including the variable time interval of variable duration and at least one additional time interval having a lower variability. The additional time interval can be a constant time interval. In FIG. 2 the consistent time interval 60 and the variable time interval 50 are shown. The duration of the variable time interval is determined in step S 84 based on the physiological parameter and in step S 85 the MR images are assigned to different cardiac phases taking into account the duration of the variable time interval and the duration of the cardiac cycle in each of the cardiac cycles.

In connection with FIGS. 5 to 11 methods are discussed in further detail how the parameters governing the separation into the three regions I to III of each cycle shown in FIG. 3 could be found.

A diagnostic ECG contains multiple waves during the cardiac cycle: the QRS complex that indicates the electrical activation of the ventricular contraction, the T wave that indicates the end systolic "repolarization" interval of the ventricle and late in the cardiac cycle the P wave that indicates the start of the atrial contraction. These waves can be used as markers to separate the weakly and strongly scaling cardiac cycle intervals. The P-wave corresponds to the start of the weakly scaling interval, but there is no clear electric activity marking the precise end of this interval (approximately around the end of the T-wave). Therefore, even a diagnostic quality ECG could not be used by itself to determine the model parameters.

The linear scaling interval ('ventricular diastasis') is starting with the end of the ultra-sound E-wave and ends with the start of the ultra-sound A-wave. Therefore, an ultrasound measurement would provide the information we are interested in. However, it is highly challenging to obtain ultra-sound compatibly with MRI and it is far from routinely available in commercial MR scanners.

In the MRI environment, the ECG is degraded as explained below, and is conventionally used only to generate a trigger signal at the R-wave of the cardiac cycle. Thus, its quality can be limited and typically only the R-wave is routinely detected; however, the other components present in the signal may yield valuable information about the patient's cardiac cycle as well.

Detrimental effects that generate additional artefact waves on the ECG are:
  MRI gradient pulses that generate spike-like signal that obscures subtle signals. This is especially problematic for non-periodic sequences with strong spoiler or encoding gradients (e.g., for diffusion or other preparation pulses). They are present only during measurements and for many measurements, especially the cine and cine flow scans, their contribution to the signal is approximately constant and thus negligible.
  The strong static magnetic field of the magnet in an MRI scanner leads to the magneto hydro dynamic effect (MHD): Flowing blood across the magnetic field will generate an electric field that is proportional to the flow velocity, which always but with varying amplitude is detected in the ECG channels. The MHD is superimposed on the true ECG signal and presents itself as a series of extra pulses or oscillations during each normal cardiac cycle. This effect increases with field strength: it is visible at 1.5 T, but at 3 T can reach amplitudes comparable to the R-wave amplitude. In triggering algorithms the R-wave can be detected despite these effects because the R-wave is usually sharper in time. The strength of voltage detected from each major pulse of blood flow depends on its angle to B0 and the conductance from its location to the ECG pads, which will be further convoluted with variations in patient anatomy as well. Historically, in cardiac MRI these MHD pulses have previously been dismissed as a nuisance only that renders detailed features of the ECG in MR systems non-diagnostic.

Therefore, the MHD effect on the ECG does not necessarily originate in the heart itself, but can represent a superimposed voltage originating from blood in the blood vessels, which is induced by its flow in the main B0 magnetic field.

One idea is that any contribution in the ECG that is related to cardiac motion can be used to identify the scaling and constant intervals of cardiac motion during each individual cardiac cycle, as measurement data for the respective cardiac cycle becomes available, i.e. beat-to-beat. Gradient induced spikes are not directly linked to cardiac motion, but MHD is. Thus, the normally unwanted MHD can be used for this purpose. Together with the "true" ECG-waves it will provide a signal that can be analyzed to determine the interpolation model parameters.

Note on timing relationship of MHD and cardiac tissue motion: pulse wave velocity delays parts of the signal coming from aortic arch across B0 and usually the strongest signal by worst case 40 ms. However the main pulmonary artery flow also partially crosses B0, as do the smaller left and right branch PAs (though these perhaps have less "contact tissue" pathways towards the ECG pads), and further in a "horizontal heart" the ventricular outflows may be more across B0 than in some other patients. Thus, the detailed relationship of MHD and cardiac tissue motion is highly variable per subject and ECG pad positioning, but limited to delays that are typically smaller than the time resolution of the clinical Cine measurement to be corrected.

If a model for the scaling rule is assumed, e.g. equation [3], then the task is to find the free parameters of the model for each cardiac cycle of raw data that is assembled to complete the required raw data coverage. This can be achieved by recording ECG data over several heart beats, either during a measurement or during scanner idle times. If the recorded data contains cardiac cycles of different length, the ECG data for these cycles can be compared using cross correlation after applying the scaling rule. The simplest way to find the correct value for the free parameters is to do this comparison for all possible combinations of free parameter values and identify the combination that results in the highest correlation values.

Figure 5:
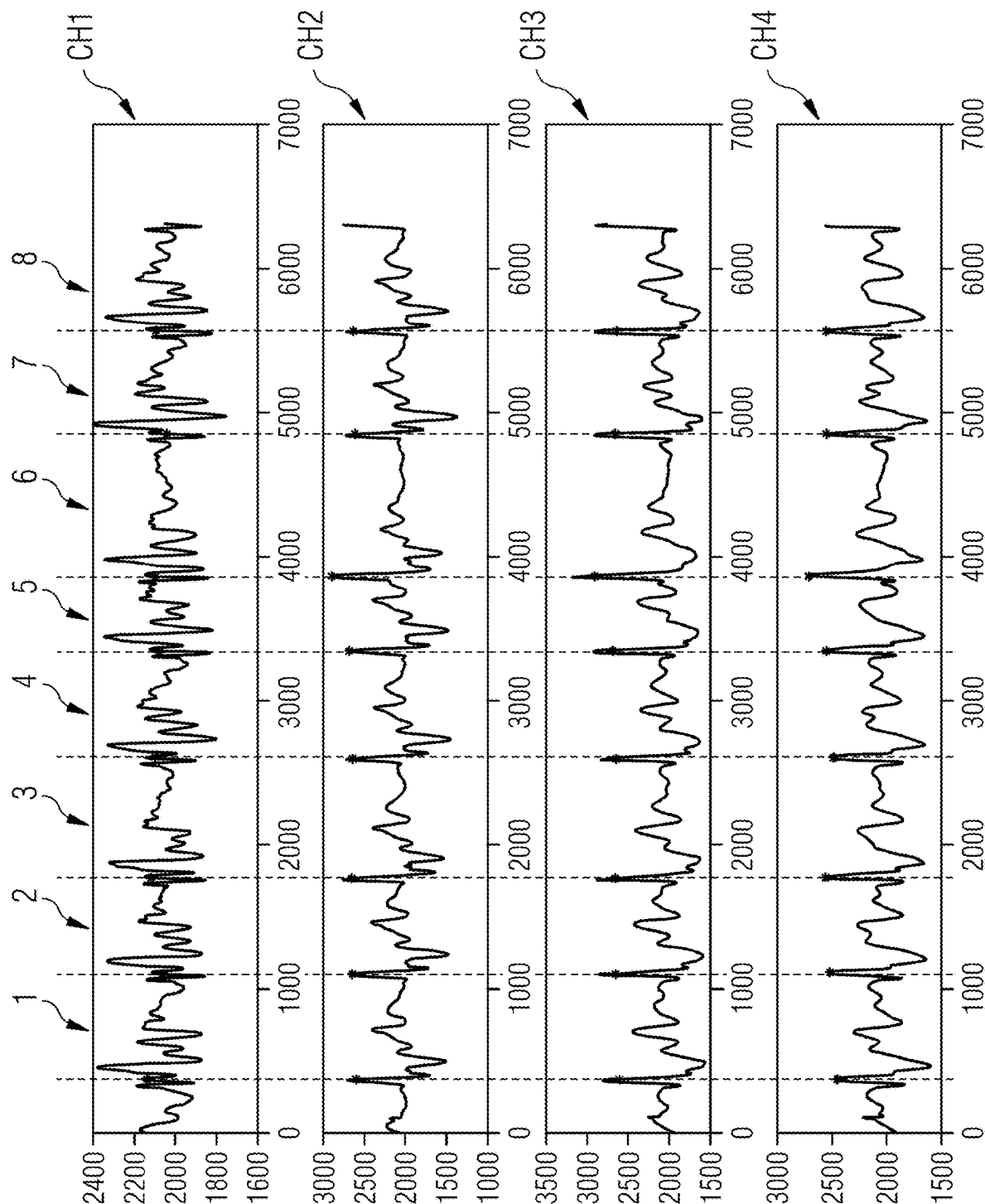
FIG. 5 schematically illustrates ECG measurement signals over eight cardiac cycles of four ECG channels, according to embodiments of the present disclosure.

FIG. 5 schematically illustrates ECG measurement signals over eight cardiac cycles 1-8 of four ECG channels CH1, CH2, CH3, CH4, according to embodiments of the present disclosure.

Measurement data values of these example time series are plotted against time in ms, wherein dotted lines indicate the trigger time point of each cardiac cycle. The magneto-hydrodynamic effect is visible in all four channels CH1, CH2, CH3, CH4. As can be seen, the cardiac cycles 1-8 exhibit strongly varying cardiac cycle durations, wherein 5 is shortened and beat 6 prolonged.

Figure 6:
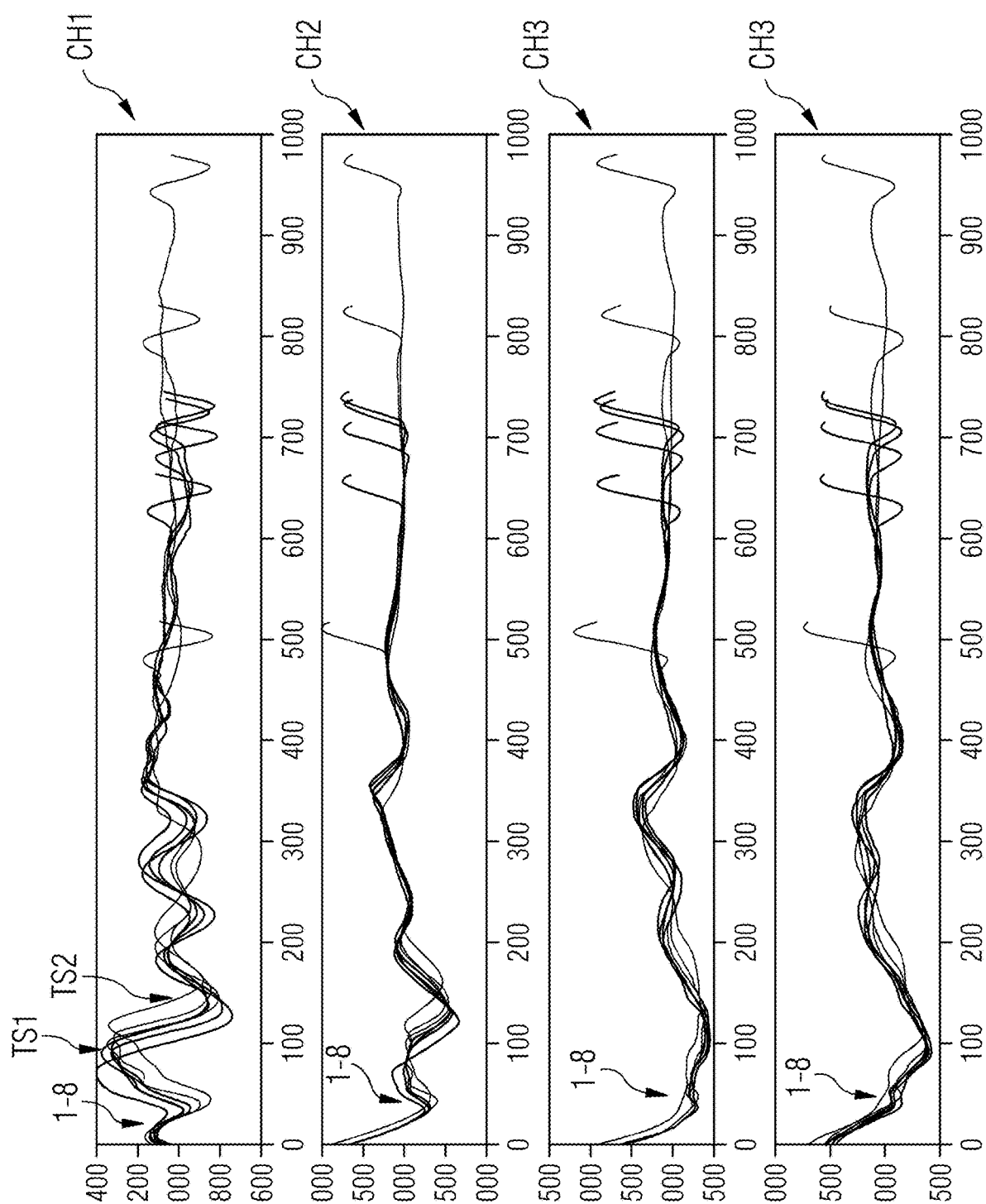
FIG. 6 schematically illustrates the superimposed measurement signals of the cardiac cycles of the four ECG channels, according to embodiments of the disclosure.

FIG. 6 schematically illustrates the superimposed measurement signals of the cardiac cycles 1-8 of the four ECG channels CH1, CH2, CH3, CH4.

As can be seen in FIG. 6, a plot of these signals relative to the R-wave, i.e. all cardiac cycles are plotted on top of each other, wherein the last incomplete heart beat has been omitted, and the data values are plotted against time-after trigger in ms. Two of the signals are marked as TS1 and TS1, and may refer to any two time series that can be used to train a model according to the present disclosure.

Figure 7:
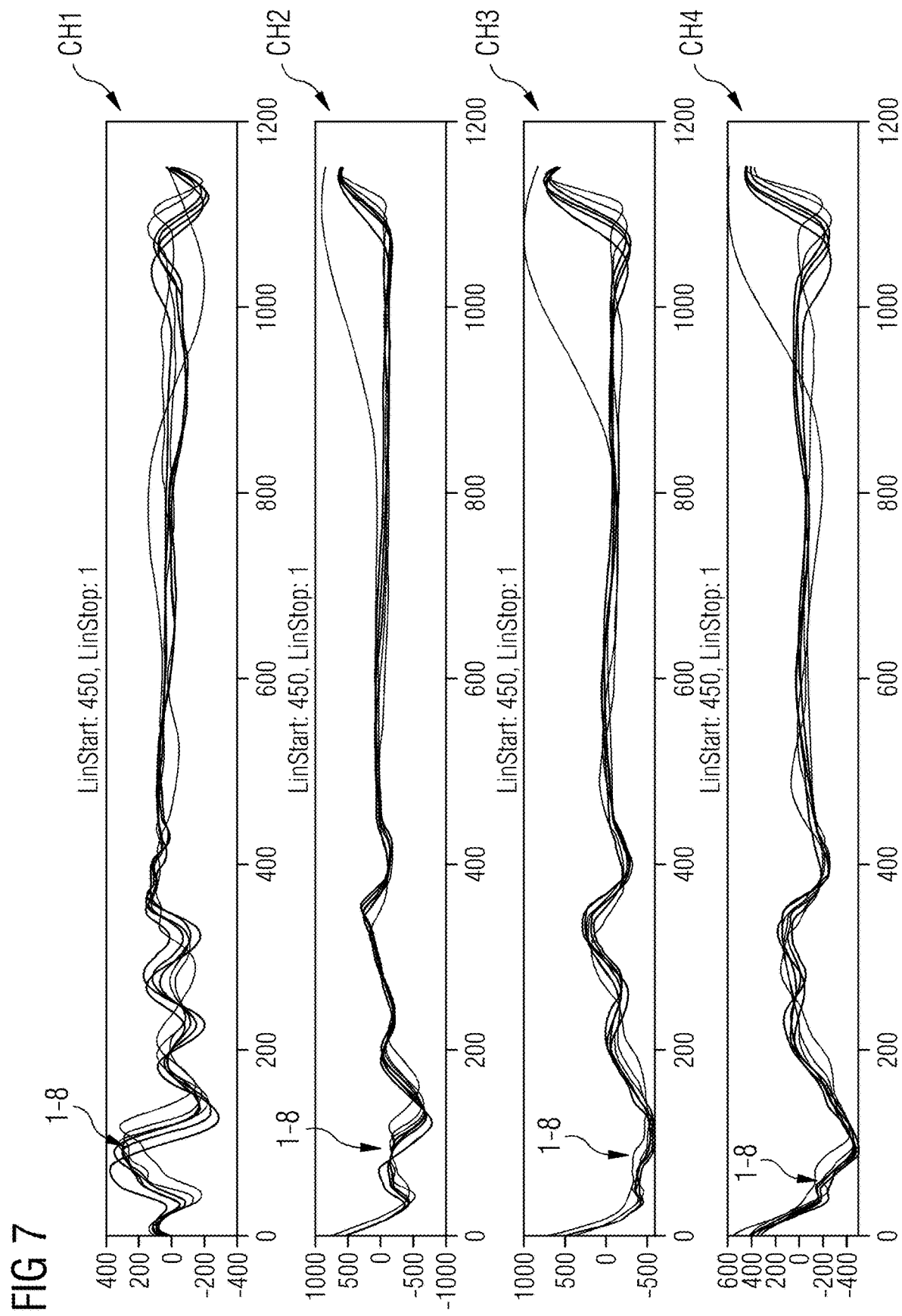
FIG. 7 schematically illustrates the superimposed measurement signals of the cardiac cycles after linear interpolation of each entire cardiac cycle to an average (i.e. reference) cardiac cycle according to at least one example embodiment.

FIG. 7 schematically illustrates the superimposed measurement signals of the cardiac cycles 1-8 after linear interpolation of each entire cardiac cycle to an average (i.e. reference) cardiac cycle.

The last incomplete heart beat has been omitted, and the data is plotted after interpolation against time after trigger in an average cardiac cycle.

Figure 8:
FIG. 8 schematically illustrates the superimposed measurement signals of the cardiac cycles after linear interpolation with a fixed (i.e. not temporally scaled) 450 ms region at the start and a 50 ms fixed region before the end of each cardiac cycle according to at least one example embodiment.

FIG. 8 schematically illustrates the superimposed measurement signals of the cardiac cycles after linear interpolation with a fixed (i.e. not temporally scaled) 450 ms region at the start and a 50 ms fixed region before the end of each cardiac cycle, according to embodiments of the disclosure.

Figure 9:
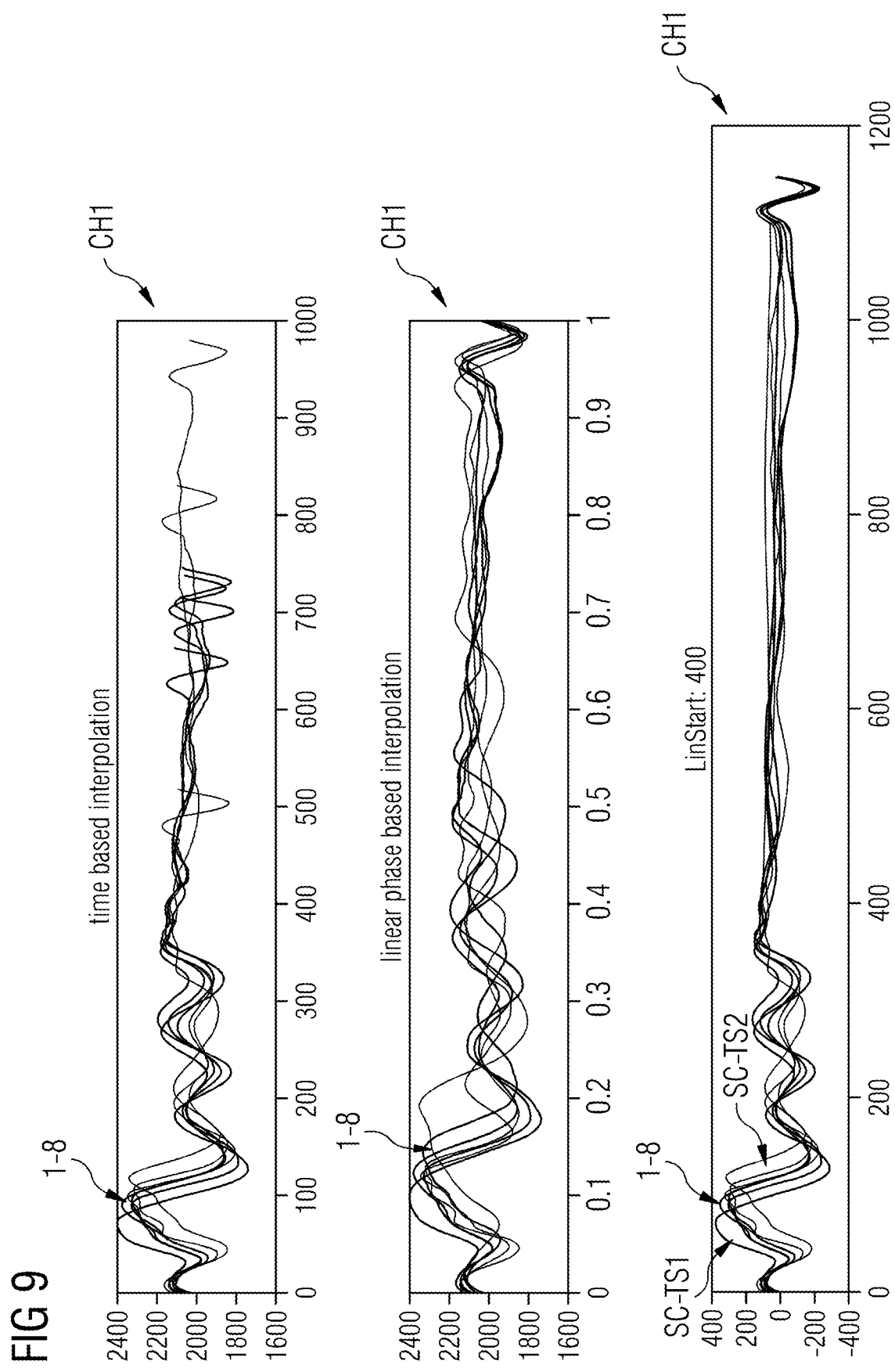
FIG. 9 schematically illustrates the superimposed measurement signals of the cardiac cycles of channel 1, without interpolation (as in FIG. 5), after linear interpolation (as in FIG. 6), and after linear interpolation starting after 400 ms from the beginning of each cardiac cycle and with a 50 ms stop region before the end of each cardiac cycle according to at least one example embodiment.

FIG. 9 schematically illustrates the superimposed measurement signals of the cardiac cycles of channel 1, without interpolation (as in FIG. 5), after full-cycle linear interpolation (as in FIG. 6), and after linear interpolation starting after 400 ms from the beginning of each cardiac cycle and with a 50 ms stop region before the end of each cardiac cycle, according to embodiments of the disclosure.

Two of the scaled measurement signals after linear interpolation starting after 400 ms from the beginning of each cardiac cycle and with a 50 ms stop region before the end of each cardiac cycle are marked as SC-TS1, correlating to the measurement signal TS1 of FIG. 2, and SC-TS2, correlating to the measurement signal TS2 of FIG. 2.

The data demonstrates that a weakly scaling interval I is identifiable in the data in all channels, and that the weakly scaling interval III is identifiable in the data in all channels. The signals for the shortest and longest cardiac cycle 5 and 6 deviate from the signals for the other cardiac cycles. This difference could be used to separate arrhythmic from regular heart beats.

Additional Info by Vectorcardiography (VCG):

This ECG MHD information may be further identified using the VCG method of analyzing the multiple electrical channels recorded. The "direction" of MHD waves may assist in separating strongly delayed ones from ones more faithfully following cardiac motion, improving the parameter quality.

Additional Use of the MHD Effect Using VCG:

The separation of different MHD waves by VCG may also help identify certain kinds of abnormal beats of the heart such as ventricular ectopic beats. Specifically, the difference between ECG outside the field and within the field might be supportive of one or more example embodiments. The ECG is already recorded outside the B0 field by the "training" stage which by rerunning inside B0 with no scan running (i.e. not overwriting the same training data, keeping this separate—unlike the current product) could provide that difference information. (However, a possible limitation may require attention because it is widely believed that the changing ECG pad skin contact resistance during a long CMR scan can alter the channel distributions of the ECG signal as the scan proceeds.)

The disclosed techniques newly employ MHD signals in the ECG that have previously been discarded, which contain cardiac blood flow data that may assist in combination with the conventional R-wave detection for optimizing non-uniform scaling of retrogated cine data.

This information can be gained during the scan to be corrected or from ECG data taken in the magnet before the scan.

Alternatively, the interpolation parameters could be obtained from motion information strongly present in the cardiac "Pilot Tone" data as described in EP 3 413 075 A1 and related ID). To optimize the interpolation of retrogated cines one could employ cardiac PT information in combination with the above MHD information and with the conventional ECG trigger. For example, ECG-R-wave based triggering could be used while PT data and optionally MHD could be used to derive interpolation information.

Figure 10:
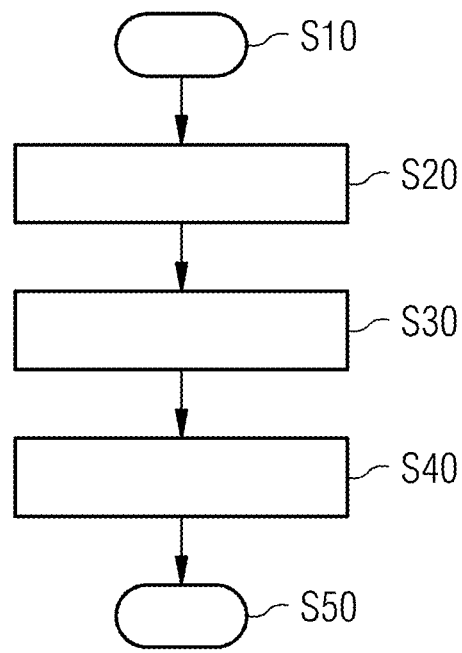
FIG. 10 schematically illustrates a flowchart with steps for determining model parameters for cardiac phase interpolation, according to embodiments of the present disclosure.

FIG. 10 schematically illustrates a flowchart with steps for determining model parameters for cardiac phase interpolation, according to embodiments of the present disclosure.

The method starts in step S10. In step S20, a first time series of data values associated with a first cardiac cycle is received. In step S30, the first time series is scaled to a reference time length of a reference cardiac cycle, wherein scaling comprises applying a model to the first time series, in order to generate a first scaled time series of data values associated with the first cardiac cycle. In step S40, the model parameters are determined using the first scaled time series, in particular a difference between the first scaled time series and another time series, such as the reference time series or another scaled time series. The method ends in step S50.

Figure 11:
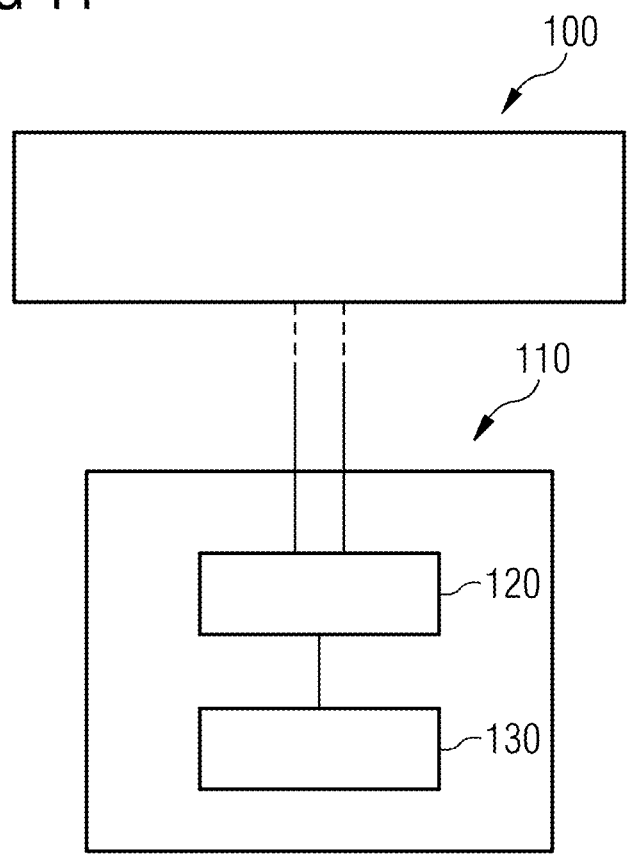
FIG. 11 schematically illustrates a medical system with which the methods for determining model parameters for cardia phase interpolation may be carried out, according to embodiments of the present disclosure.

FIG. 11 schematically illustrates a medical system 100 with which the methods for determining model parameters for cardiac phase interpolation may be carried out, according to embodiments of the present disclosure.

A medical system 100 comprises a control unit 110 including a processing unit 120 and a memory unit 130, wherein the memory unit 30 stores control information executable by the processing unit 120, and wherein, when executing of the control information in the processing unit 120, the medical system 100 is configured to perform a method according to the present disclosure.

Advantages of the Disclosed Techniques Include:

Cardiac phase interpolation is optimized for the individual patient automatically without the need for the user to repeat the measurement with multiple parameter settings. This will result in improved image quality in the presence of varying heart rate for retrogated cine images.

Evaluations that are based on multiple measurements, e.g., ventricular function, will have more consistent input data, thus should be more reliable in case of varying heart rate.

Detailed aspects of cardiac function such as wall motion abnormalities, valve disorders and atrial function will be imaged with increased reliability as many patients exhibit variations in R-R interval due to arrhythmia or associated with breath-hold maneuvers.

The optimized interpolation rule can be applied to subsequent measurements, e.g., to automatically place the acquisition into the mid-diastolic interval and keep it there for slowly changing heart rates.

In disease, there is very often mechanical dyssynchrony of ventricular contraction and relaxation. one or more example embodiments yield improvements to cine imaging compared to the conventional cine retrogating method. Further, the dyssynchrony is quite often subtle and small, even difficult for clinicians to be certain of, and so one or more example embodiments improve retrogated cine imaging so that these small dyssynchronous perturbations to uniform cardiac contractility and relaxation might be made more visible.

From the above said, some general conclusions may be drawn:

Various techniques according to the present disclosure may provide for identification of cardiac phases, wherein a measurement signal characterized or dominated by an MHD effect may be used.

The first and the second time series of data values may be Electrocardiography (ECG) measurement signals of a patient, wherein each time series includes a different cardiac cycle. The time series may include signal characteristics of a Magnetohydrodynamic (MHD) effect in a patient, and may be representative of a cardiac motion. The time series of data values representative of a cardiac motion or measurement signal may consist of, or represent, or be predominantly characterized by a Magnetohydrodynamic (MHD) effect in the blood vessels of a patient.

The first and second cardiac cycles may be chronologically directly sequential cardiac cycles.

Scaling the first and/or the second time series to a reference time length of a reference cardiac cycle may comprise adapting time values associated with the data values. In various examples, the time series of each cardiac cycle is scaled to match that of the reference cycle.

The first and/or the second scaled time series may have the same cardiac cycle time length, after applying the model, as the reference cardiac cycle.

In addition to the first and the second time series, a plurality of further time series associated with a respective one of a plurality of further cardiac cycles may be used to train the model, in particular each including a different cardiac cycle with a varying, i.e. different, cardiac cycle length. The model may be applied to each of the plurality of time series, as the time series become available during measurement, in order to determine a cardiac phase interpolation model for the respective cycle.

The reference cardiac cycle may be a mean, median, minimum, maximum cardiac cycle length of the plurality of cardiac cycles used for determining the model parameters.

The method may further comprise interpolating at least one of the first and the second scaled time series, wherein interpolating comprises generating new data values for corresponding new time values.

In various example, the first unscaled time series may contain the measured data for the first cardiac cycle. By applying the model, the first scaled time series is obtained, which is scaled to have the same time length as the reference cardiac cycle. In this regard, the model may be the scaling rule onto the reference cardiac cycle. After the scaling by applying the model, the data may already lie on a reference time grid, for example of the reference cardiac cycle, but in various examples data points may not lie on the reference time grid. In this case, the data of two cardiac cycles must first be interpolated to a common time grid, usually the reference time grid, before determination of a difference between the time series may be performed. In general, the scaling model may map to a reference time grid, specifically that of the reference heartbeat, i.e. it may comprise the necessary interpolation as an optional step. It is to be understood that this optional interpolation onto the reference time grid may be performed with the scaled and unscaled time series.

A difference between the first and the second scaled time series may comprise a difference between corresponding data values, i.e. which have the same time or index value.

The model may be referred to as a cardiac cycle interpolation model.

The time series of data values may represent or may be characterized by a cardiac motion, in particular an Electrocardiography (ECG) measurement signal or an PilotTone reference signal representing cardiac movement in an MRI measurement.

Determining model parameters may comprise adapting at least one model parameter to minimize a difference between the first and/or second scaled time series and/or the time series of measurement data values of the reference cardiac cycle.

Applying the model to a time series of data values may modify a time period defined between the first data value and the time value and the last time value in the time series.

The time series of data values may be acquired, and/or the determining of the model parameters for cardiac phase interpolation may be performed, during per cycle adaptation of the acquired data for each cycle of an MRI imaging method.

The model parameters may be determined, in order to minimize the difference between the first and/or second and/or the time series of data points associated with the reference cardiac cycle.

The method may further comprise determining a cardiac phase using the model, for example applying the model to a time value, which may be a time after trigger of a cardiac cycle, in order to provide a scaled time value as output, and/or identifying a cardiac phase of the cardiac cycle based on the scaled, or scaled, time value.

In various examples, the model may be used for comparing two time values of different cardiac cycles, wherein by applying the trained model to one or more time values, the time values may be on the same time scale and may be directly compared. In such a way, when two scaled time values, which may be associated with respective measurement data, may be the same or may be in a predefined time window/period, the two time values may be associated with the same cardiac phase.

In various examples, the model may be applied to an MRI data set, in order to associate different subset of the MRI dataset to specific cardiac phases.

The model may receive as input a duration of the reference cardiac cycle, e.g. as defined by trigger time points determined based on a heart beat signal, for example a characteristic wave of an ECG signal, specifically the R wave of the cardiac cycles. The model may receive as input a time series of data values of the reference cardiac cycle, which may be a time series of averaged data values over a plurality of cardiac cycles.

A model may be used to determine a cardiac phase, wherein the model modifies a time value, which may be a time after trigger of a heart beat signal, for example a periodic signal such as an ECG signal. The time point, which may be a time after trigger, may be scaled using/by the same model, which is used for scaling/modifying the time series of data values associated with a cardiac cycle.

The parameters governing the model (i.e. the fixed and varying fraction timings within each beat) may be repeatedly adjusted before and/or during and/or after a measurement process, which may be the measurement process generating the time series for training the model or a measurement process, such as an MRI measurement process, in which the trained model is used for determining a cardiac phase.

The time series representative of a cardiac motion may be acquired and/or the training of the model for cardiac phase interpolation may performed per cycle to an MRI imaging method. In such a way, the model may be determined per cycle, i.e. for each cycle.

In a method for acquiring an MRI image of a heart, a MRI image may be associated with a cardiac phase using a scaled time value determined by a method according to the present disclosure.

Summarizing, a method is provided for training a model for cardiac phase interpolation comprising beat to beat parameter optimisation for each individual cardiac cycle required to complete the scan, which enable fast and reliable identification of cardiac phases by using a plurality of values of a measurement signal encoding a movement of a heart during a cardiac cycle.

One or more example embodiments of the present invention fully utilises existing knowledge about which sections of the cardiac cycle change most with heart rate.

Furthermore, one or more example embodiments of the present invention is not limited to ECG R-wave triggering but works for all trigger time points outside the diastasis interval.

One or more example embodiment of the present invention combines all information available in the scanner about real-time beat-to-beat physiology to optimally and individually adjust the durations of the sections considered above for each cycle of raw data used.

One or more example embodiment of the present invention minimizes image artefacts from inaccuracies in the applied interpolation by an optimized forward-backward interpolation strategy.

An advantage of the invention is an improved image quality in ECG, Pilot Tone, PPG, or acoustically triggered retrogated cines (MR images). This is especially relevant for clear imaging of late diastolic events, ventricular filling and wall motion abnormalities, valve leaflets and flow disturbances, and atrial imaging. A further advantage is an improved accuracy of quantitative flow and volumetric results.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/ or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'unit', interface' or the term 'controller' may be replaced with the term 'circuit.' The term 'module' and may 'unit' refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention is not limited to the example embodiment described hereintofore. Rather, other variants of the invention can also be derived herefrom by the person skilled in the art, without departing from the subject matter of the invention. In particular, it is furthermore possible to combine all the individual features described in connection with the example embodiment with one another in a different way also, without departing from the subject matter of the invention.

The invention claimed is:

1. A method for assigning MR images of a heart obtained at a plurality of cardiac cycles to different cardiac phases of the cardiac cycles, the method comprising:
   determining a heart beat signal during acquisition of the MR images obtained at the plurality of cardiac cycles;
   determining at least one physiological parameter of the heart during acquisition of the MR images obtained at the plurality of cardiac cycles;
   determining a model for the cardiac cycle, the determining the model including,
      determining, in each of the cardiac cycles, a variable time interval of variable duration and at least one additional time interval based on the heart beat signal and the at least one physiological parameter, the at least one additional time interval having a lower variability in duration than the variable time interval;
   determining a duration of the variable time interval and a duration of the cardiac cycle for each of the cardiac cycles based on the heart beat signal and the at least one physiological parameter; and
   assigning the MR images to the different cardiac phases based on the duration of the variable time interval and cardiac cycle in each of the cardiac cycles.

2. The method of claim 1, wherein the determining the at least one physiological parameter determines the at least one physiological parameter based on a magneto-hydrodynamic effect of blood flow occurring in each of the plurality of cardiac cycles.

3. The method of claim 2, wherein the heart beat signal is an ECG signal, and the determining the duration of the variable time interval includes,
   determining an end of an early passive filling of a ventricle in a diastole and a first particular time interval between a Q wave of the ECG signal and the early passive filling of the ventricle, wherein the duration of the variable time interval is based on the first particular time interval.

4. The method of claim 3, wherein the determining the duration of the variable time interval includes,
   determining a second particular time interval between a P wave and the Q wave of the ECG signal.

5. The method of claim 4, wherein the determining the variable time interval determines the variable time interval based on a corresponding cycle duration of a total cardiac cycle minus a duration of the determined at least one additional time interval for each of the cardiac cycles.

6. The method of claim 5, wherein the determining the model includes,
   for each of the cardiac cycles, determining a total duration of the cardiac cycle based on R waves in an ECG signal, wherein the total duration comprises two interpolation periods of constant duration and the variable time interval, wherein the determining the duration of the variable time interval determines the duration of the variable time interval based on the duration of the two interpolation periods and the total duration.

7. The method of claim 4, wherein the determining the duration of the variable time interval includes,
   determining a third particular time interval between the Q wave of the ECG signal of the heart and an R wave of the ECG signal as a start point of a duration of at least one of the cardiac cycles, wherein the determining the duration of the variable time interval determines the variable time interval based on the third particular time interval.

8. The method of claim 4, wherein the determining the at least one additional time interval determines the at least one additional time interval based on the first particular time interval and the second particular time interval.

9. The method of claim 8, wherein the determining the duration of the variable time interval includes,
   determining a third particular time interval between the Q wave of the ECG signal of the heart and an R wave of the ECG signal as a start point of a duration of the cardiac cycle, wherein the determining the duration of the variable time interval determines the variable time interval based on the third particular time interval.

10. The method of claim 8, wherein the determining the variable time interval determines the variable time interval based on a corresponding cycle duration of a total cardiac cycle minus a duration of the determined at least one additional time interval for each of the cardiac cycles.

11. The method of claim 8, wherein the determining the at least one additional time interval determines the at least one additional time interval based on a combination of the first particular time interval and the second particular time interval.

12. The method of claim 11, wherein the determining the model includes,
  for each of the cardiac cycles, determining a total duration of the cardiac cycle based on R waves in an ECG signal, wherein the total duration comprises two interpolation periods of constant duration and the variable time interval, wherein the determining the duration of the variable time interval determines the duration of the variable time interval based on the duration of the two interpolation periods and the total duration.

13. The method of claim 1, wherein the determining the variable time interval includes,
  determining a Diastasis as one of the cardiac phases in the cardiac cycle.

14. The method of claim 13, wherein the determining the model includes,
  for each of the cardiac cycles, determining a total duration of the cardiac cycle based on R waves in an ECG signal, wherein the total duration comprises two interpolation periods of constant duration and the variable time interval, wherein the determining the duration of the variable time interval determines the duration of the variable time interval based on the duration of the two interpolation periods and the total duration.

15. The method of claim 1, wherein the determining the at least one physiological parameter determines the at least one further physiological parameter based on at least one of an ECG signal, a pilot tone, acoustic signals of the heart, and the MR images obtained from the heart.

16. The method of claim 1, wherein the determining the model includes,
  for each of the cardiac cycles, determining a total duration of the cardiac cycle based on R waves in an ECG signal, wherein the total duration comprises two interpolation periods of constant duration and the variable time interval, wherein the determining the duration of the variable time interval determines the duration of the variable time interval based on the duration of the two interpolation periods and the total duration.

17. The method of claim 16, wherein the duration of the two interpolation periods is based on a first particular time interval between a Q wave of the ECG signal and an early passive filling of a ventricle, a second particular time interval between a P wave and the Q wave of the ECG signal and a third particular time interval between the Q wave of the ECG signal of the heart and an R wave of the ECG signal.

18. A non-transitory computer readable medium comprising program code that, when executed by at least one processor, causes the at least one processor to carry out the method of claim 1.

19. A non-transitory computer readable medium comprising program code that, when executed by at least one processor, causes the at least one processor to carry out the method of claim 2.

* * * * *